US009278140B2

(12) United States Patent
Hunt

(10) Patent No.: US 9,278,140 B2
(45) Date of Patent: Mar. 8, 2016

(54) SUSTAINED RELEASE POLOXAMER CONTAINING PHARMACEUTICAL COMPOSITIONS

(71) Applicant: Allergan, Inc., Irvine, CA (US)

(72) Inventor: Terrence J. Hunt, Temecula, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/827,665

(22) Filed: Aug. 17, 2015

(65) Prior Publication Data

US 2015/0352226 A1 Dec. 10, 2015

Related U.S. Application Data

(62) Division of application No. 12/036,139, filed on Feb. 22, 2008, now Pat. No. 9,107,815.

(51) Int. Cl.

| | |
|---|---|
| A61K 39/08 | (2006.01) |
| A61K 38/48 | (2006.01) |
| A61K 47/48 | (2006.01) |
| A61K 8/66 | (2006.01) |
| A61K 9/00 | (2006.01) |
| A61K 8/04 | (2006.01) |
| A61K 8/64 | (2006.01) |
| A61K 8/90 | (2006.01) |
| A61Q 19/08 | (2006.01) |
| A61K 41/00 | (2006.01) |

(52) U.S. Cl.
CPC ........... *A61K 47/48784* (2013.01); *A61K 8/042* (2013.01); *A61K 8/64* (2013.01); *A61K 8/66* (2013.01); *A61K 8/90* (2013.01); *A61K 9/0024* (2013.01); *A61K 38/4893* (2013.01); *A61K 41/00* (2013.01); *A61K 47/48215* (2013.01); *A61K 47/48284* (2013.01); *A61Q 19/08* (2013.01); *A61K 2800/52* (2013.01); *A61K 2800/56* (2013.01); *A61K 2800/594* (2013.01); *A61K 2800/91* (2013.01); *A61K 2800/95* (2013.01); *C12Y 304/24069* (2013.01)

(58) Field of Classification Search
CPC .......................... A61K 39/08; A61K 38/4893
USPC ....................... 424/239.1; 514/17.7
See application file for complete search history.

(56) References Cited

U.S. PATENT DOCUMENTS

| | | | |
|---|---|---|---|
| 4,806,337 A | 2/1989 | Snipes et al. ............... 504/360 |
| 5,252,318 A | 10/1993 | Joshi et al. ................ 424/78.04 |
| 5,278,201 A | 1/1994 | Dunn et al. .................. 523/113 |
| 5,512,547 A | 4/1996 | Johnson et al. | |
| 5,516,703 A | 5/1996 | Caldwell et al. ............. 436/532 |
| 5,667,808 A | 9/1997 | Johnson et al. | |
| 5,696,077 A | 12/1997 | Johnson et al. | |
| 5,756,468 A | 5/1998 | Johnson et al. | |
| 5,914,334 A | 6/1999 | Charu ........................ 514/337 |
| 5,980,945 A | 11/1999 | Ruiz | |
| 6,007,843 A | 12/1999 | Drizen et al. | |
| 6,011,011 A | 1/2000 | Hageman | |
| 6,022,554 A | 2/2000 | Lee et al. | |
| 6,087,327 A | 7/2000 | Pearce et al. | |
| 6,306,423 B1 | 10/2001 | Donovan et al. | |
| 6,312,708 B1 | 11/2001 | Donovan | |
| 6,316,011 B1 | 11/2001 | Ron et al. .................. 424/401 |
| 6,465,425 B1 | 10/2002 | Tracy et al. ................ 514/13.7 |
| 6,565,888 B1 | 5/2003 | Tracy et al. ................ 424/489 |
| 6,649,702 B1 | 11/2003 | Rapoport et al. ............ 525/299 |
| 6,773,711 B2 | 8/2004 | Voet et al. ................. 424/239.1 |
| 7,097,857 B2 | 8/2006 | Tracy et al. ................ 424/489 |
| 7,140,371 B2 | 11/2006 | Hanin et al. ................ 128/898 |
| 7,211,261 B1 | 5/2007 | Moyer et al. .............. 424/236.1 |
| 7,579,010 B2 | 8/2009 | Hunt ......................... 424/236.1 |
| 7,758,873 B2 | 7/2010 | Hunt ......................... 424/247.1 |
| 7,780,967 B2 | 8/2010 | Hunt ......................... 424/236.1 |
| 7,829,525 B2 | 11/2010 | Frevert ...................... 514/13.7 |
| 8,137,677 B2 | 3/2012 | Hunt ......................... 424/234.1 |
| 8,168,206 B1 | 5/2012 | Hunt ......................... 424/247.1 |
| 8,173,138 B2 | 5/2012 | Moyer et al. .............. 424/236.1 |
| 8,632,785 B2 | 1/2014 | Hunt ......................... 424/247.1 |
| 8,642,047 B2 | 2/2014 | Hunt ......................... 424/234.1 |
| 8,816,591 B2 | 8/2014 | Chu et al. ................... 424/247.1 |
| 8,877,208 B2 | 11/2014 | Baker et al. ................ 424/203.1 |

(Continued)

FOREIGN PATENT DOCUMENTS

| | | |
|---|---|---|
| CN | 1 215 084 | 4/1999 |
| EP | 1 112 082 | 7/2002 |

(Continued)

OTHER PUBLICATIONS

U.S. Appl. No. 11/524,683, filed Nov. 21, 2006, Hunt.
U.S. Appl. No. 11/954,602, filed Dec. 12, 2007, Tezel et al.
U.S. Appl. No. 11/954,629, filed Dec. 12, 2007, Blanda et al.
Carpenter, et al.; Interactions of Stabilizing Additives with Proteins During Freeze-Thawing and Freeze-Dying, International Symposium on Biological Product Freeze-Drying and Formulation, Oct. 24-26, 1990; Karger (1992), 225-239.
Dumortier, Gilles; et al.: A Review of Poloxamer 407 Pharmaceutical and Pharmacological Characteristics. Pharmaceutical Research, vol. 23, No. 12, Dec. 2006. pp. 2709-2728.
Garry, Mary; et al.: Evaluation of the Efficacy of a Bioerodible Bupivacaine Polymer System on Antinociception and Inflammatory Mediator Release. Pain 82(1999), pp. 49-55.

(Continued)

*Primary Examiner* — Albert Navarro
*Assistant Examiner* — Ginny Portner
(74) *Attorney, Agent, or Firm* — Brigitte C. Phan; Ted A. Chan

(57) ABSTRACT

A thermo-reversible thermoplastic pharmaceutical composition, comprising a botulinum toxin and a biocompatible poloxamer which provides thermoreversibility to the composition and additionally stabilizes the botulinum toxin, is described. The pharmaceutical composition can be administered to a patient as a liquid, and gels after administration into a sustained release drug delivery system from which the biologically active botulinum toxin is released over a multi-day period thereby localizing the drug as a depot and controlling release to enhance the therapeutic effect per dose.

9 Claims, No Drawings

(56) References Cited

U.S. PATENT DOCUMENTS

| | | | |
|---|---|---|---|
| 2003/0092776 A1 | 5/2003 | Ron et al. | 514/772.6 |
| 2003/0118598 A1 | 6/2003 | Hunt | |
| 2003/0133980 A1 | 7/2003 | Costantino et al. | 424/468 |
| 2004/0009180 A1 | 1/2004 | Donovan | 424/184.1 |
| 2004/0156906 A1 | 8/2004 | Ding et al. | 424/486 |
| 2004/0247623 A1 | 12/2004 | Cady | 424/239.1 |
| 2005/0025778 A1 | 2/2005 | Cormier et al. | 424/185.1 |
| 2005/0025830 A1 | 2/2005 | Bruinewoud et al. | 424/472 |
| 2005/0123550 A1 | 6/2005 | Laurent et al. | 424/184.1 |
| 2005/0238668 A1 | 10/2005 | Wang et al. | 424/239.1 |
| 2006/0013883 A1 | 1/2006 | Nicol et al. | 424/486 |
| 2006/0040894 A1 | 2/2006 | Hunter et al. | 514/54 |
| 2006/0078616 A1 | 4/2006 | Georgewill et al. | 424/486 |
| 2006/0104994 A1 | 5/2006 | Hunt | 424/239.1 |
| 2006/0127429 A1 | 6/2006 | McCartt et al. | 424/401 |
| 2006/0251724 A1 | 11/2006 | Farrell et al. | 424/487 |
| 2007/0077259 A1 | 4/2007 | Dake et al. | 424/239.1 |
| 2007/0134199 A1 | 6/2007 | Frevert | 424/85.4 |
| 2007/0196425 A1 | 8/2007 | Ding et al. | 424/423 |
| 2007/0237740 A1 | 10/2007 | Reddington et al. | 424/78.08 |
| 2007/0253960 A1 | 11/2007 | Roy et al. | 424/143.1 |
| 2008/0045553 A1 | 2/2008 | Wilson | 514/267 |
| 2008/0097229 A1 | 4/2008 | Roy et al. | 600/500 |
| 2008/0274194 A1 | 11/2008 | Miller et al. | 424/489 |
| 2009/0053290 A1 | 2/2009 | Sand et al. | 424/449 |
| 2009/0087457 A1 | 4/2009 | Dake et al. | 424/239.1 |
| 2009/0131889 A1 | 5/2009 | Oronsky et al. | 604/290 |
| 2009/0186081 A1 | 7/2009 | Holm et al. | 424/464 |
| 2009/0258924 A1 | 10/2009 | Lyons et al. | 514/44 A |
| 2009/0264385 A1 | 10/2009 | Crowley et al. | 514/165 |
| 2010/0150994 A1 | 6/2010 | Kotyla | 424/449 |
| 2010/0279953 A1 | 11/2010 | Hunt | 514/21.2 |
| 2010/0291226 A1 | 11/2010 | Mazzone et al. | 424/523 |
| 2011/0106021 A1 | 5/2011 | Ruegg et al. | 604/290 |
| 2012/0082717 A1 | 4/2012 | Char et al. | 424/450 |
| 2012/0122802 A1 | 5/2012 | Hunt | 514/21.2 |
| 2012/0141619 A1 | 6/2012 | Hunt | 424/780 |
| 2012/0156244 A1 | 6/2012 | Horn | 424/239.1 |
| 2012/0238504 A1 | 9/2012 | Moyer et al. | 514/18.1 |
| 2012/0238969 A1 | 9/2012 | Ruegg et al. | 604/290 |

FOREIGN PATENT DOCUMENTS

| | | | |
|---|---|---|---|
| EP | 1 253 932 | 4/2005 | |
| WO | WO 01/93827 | 12/2001 | |
| WO | WO 2004/060384 | 7/2004 | |
| WO | 2004/084839 | 10/2004 | |
| WO | WO 2004/084839 | 10/2004 | |
| WO | WO 2006/020208 | 2/2006 | |
| WO | 2006/094263 | 9/2006 | |
| WO | 2007/041664 | 2/2007 | A61K 47/32 |
| WO | WO 2007/041664 | 4/2007 | |

OTHER PUBLICATIONS

Goodnough M.C., et al.; Recovery of Type-A Botulinum Toxin Following Lyophilization, ACS Symposium Series 1994;567(-):193-203.

Goodnough M.C., et al.; Stabilization of Botulinum Toxin Type A During Lyophilization, App & Envir. Micro. 58 (10) 3426-3428 (1992).

Huang K., et al.; Synthesis and Characterization of Self Assembling Block Copolymers Containing Adhesive Moieties, Polymer Preprints 2001, 42(2), 147-148.

Jeong B., et al.; Thermosensitive Sol-Gel Reversible Hydrogels, Adv. Drug Del. Rev., 54(1); 37-51, Jan. 17, 2002.

Kohl A., et al.; Comparison of the Effect of Botulinum Toxin A (Botox ®) with the Highly-Purified Neurotoxin (NT 201) in the Extensor Digitorm Brevis Muscle Test, Mov Disord 2000;15(Suppl 3):165.

Naumann, et al.; Botulinum Toxin Type A in the Treatment of Focal, Axillary, and Palmar Hyperhidrosis and Other Hyperhidrotic Conditions, European J. Neurology 6 (Supp 4):S111-S115:1999.

Powell, Elizabeth, et al.: Controlled Release of Nerve Growth Factor from a Polymeric Implant. Braun Research, 515 (1990) pp. 309-311.

Ragona, et al.; Management of Parotid Sialocele with Botulinum Toxin, The Laryngoscope 109:1344-1346:1999.

Rao, Jyoti; et al.: Implantable Controlled Delivery Systems for Proteins Based on Collagen-pHEMA Hydrogels, Biomaterials 1994, vol. 15 No. 5. pp. 383-389.

Schantz E.J., et al.; Preparation and Characterization of Botulinum Toxin Type A for Human Treatment, Chapter 3 of Jankovic, J., et al., Therapy with Botulinum Toxin, Marcel Dekker, Inc (1994).

Schantz E.J., et al.; Properties and Use of Botulinum Toxin and Other Microbial Neurotoxins in Medicine, Microbiol Rev Mar. 1992;56(1):80-99.

Stratton, L.; et al.: Drug Delivery Matrix Containing Native Protein Precipitates Suspended in a Poloxamer Gel, Journal of Pharmaceutical Science, American Pharmaceutical Association. Washington.; US, vol. 86, No. 9, Sep. 1, 1997, pp. 1006-1010.

Stratton L., et al.; Drug Delivery Matrix Containing native Protein Precipitates Suspended in a Poloxamer Gel, J. Pharm. Sci. 86(9); 1006-1010, Sep. 1996.

Stratton et al (Journal of Pharmaceutical Sciences, vol. 86, No. 9, Sep. 1997, p. 1006-1010).

SUSTAINED RELEASE POLOXAMER CONTAINING PHARMACEUTICAL COMPOSITIONS

CROSS-REFERENCES TO RELATED APPLICATIONS

This is a divisional of U.S. patent application Ser. No. 12/036,139, filed Feb. 22, 2008, which is hereby incorporated herein by reference in its entirety.

BACKGROUND

The present invention relates to thermosensitive, thermoreversible pharmaceutical compositions. In particular, the present invention relates to sustained release, gelable (thermosensitive) botulinum toxin pharmaceutical compositions formulated with a poloxamer.

A pharmaceutical composition is a formulation which contains at least one active ingredient (such as a botulinum toxin) as well as, for example, one or more excipients, buffers, carriers, stabilizers, preservatives and/or bulking agents, and is suitable for administration to a patient to achieve a desired diagnostic result or therapeutic effect. The pharmaceutical compositions disclosed herein have diagnostic, therapeutic, cosmetic and/or research utility.

For storage stability and convenience of handling, a pharmaceutical composition can be formulated as a lyophilized (i.e. freeze dried) or vacuum dried powder which can be reconstituted with a suitable fluid, such as saline or water, prior to administration to a patient. Alternately, the pharmaceutical composition can be formulated as a ready to use aqueous solution or suspension. A pharmaceutical composition can contain a proteinaceous active ingredient. Unfortunately, a protein active ingredient can be very difficult to stabilize (i.e. maintained in a state where loss of biological activity is minimized), resulting therefore in a loss of protein and/or loss of protein activity during the formulation, reconstitution (if required) and during the period of storage prior to use of a protein containing pharmaceutical composition. Stability problems can occur because of protein denaturation, degradation, dimerization, and/or polymerization. Various excipients, such as albumin and gelatin have been used with differing degrees of success to try and stabilize a protein active ingredient present in a pharmaceutical composition. Additionally, cryoprotectants such as alcohols have been used to reduce protein denaturation under the freezing conditions of lyophilization.

Thermosensitive pharmaceutical compositions, which form in-situ gels, are known. See eg U.S. Pat. No. 5,278,201. Poloxamers are nontoxic block copolymers of poly(ethylene oxide), poly(propylene oxide) and poly(ethylene oxide) (PEO-PPO-PEO). Certain poloxamers exhibit reversible thermal gelation. Thus a solution of a protein and a poloxamer prepared at low temperatures and injected will form a gel as it warms to body temperature. Subsequently the protein is slowly released from the gel. A gelable, thermo-reversible formulation comprising poloxamer 407 at a 22 wt % concentration has been prepared with the model protein drugs α-chymotrypsin and lactate dehydrogenase. Stratton L., et al., *Drug delivery matrix containing native protein precipitates suspended in a poloxamer gel*, J Pharm Sci 86(9); 1006-1010, September 1996. Formulations of certain adhesive proteins and poloxamer 127 have been made. Huang K., et al., *Synthesis and characterization of self assembling block copolymers containing adhesive moieties*, Polymer Preprints 2001, 42(2), 147-148. Additionally, poloxamer 188 and poloxamer 407 have been used an excipients in protein drug pharmaceutical compositions. Jeong B., et al., *Thermosensitive sol-gel reversible hydrogels*, Adv Drug Del Rev, 54(1); 37-51, Jan. 17, 2002. Published patent application WO 2007/041664 discloses use a pharmaceutical composition comprising a botulinum toxin and a poloxamer 188.

Botulinum toxins have been used for various therapeutic and cosmetic purposes including treating cervical dystonia, blepharospasm, strabismus, spasticity, headache, hyperhidrosis, overactive bladder, rhinitis, bruxism, enlarged prostate, achalasia, anismus, sphincter of Oddi malfunction, acne, tremors, juvenile cerebral palsy, and facial wrinkles.

Commercially available botulinum toxin containing pharmaceutical compositions include BOTOX® (Botulinum toxin type A neurotoxin complex with human serum albumin and sodium chloride) available from Allergan, Inc., of Irvine, Calif. in 100 unit vials as a lyophilized powder to be reconstituted with 0.9% sodium chloride before use), DYSPORT® (*Clostridium botulinum* type A toxin haemagglutinin complex with human serum albumin and lactose in the formulation), available from Ipsen Limited, Berkshire, U.K. as a powder to be reconstituted with 0.9% sodium chloride before use), and MYOBLOC™ (an injectable solution comprising botulinum toxin type B, human serum albumin, sodium succinate, and sodium chloride at about pH 5.6, available from Solstice Neurosciences, Inc., South San Francisco, Calif.).

Botulinum toxin is a large protein for incorporation into a pharmaceutical formulation (the molecular weight of the botulinum toxin type A complex is 900 kD) and is inherently fragile and labile. The size of the toxin complex makes it much more friable and labile than smaller, less complex proteins, thereby compounding the formulation and handling difficulties if botulinum toxin stability is to be maintained. Hence, a botulinum toxin stabilizer must be able to interact with the toxin in a manner which does not denature, fragment or otherwise detoxify the toxin molecule or cause disassociation of the non-toxin proteins present in the toxin complex.

As the most lethal known biological product, exceptional safety, precision, and accuracy are called for at all steps of the formulation of a botulinum toxin containing pharmaceutical composition. Thus, a botulinum toxin stabilizer should not itself be toxic or difficult to handle so as to not exacerbate the already extremely stringent botulinum toxin containing pharmaceutical composition formulation requirements.

Since botulinum toxin was the first microbial toxin to be approved (by the U.S. Food and Drug Administration in 1989) for injection for the treatment of human disease, specific protocols had to be developed and approved for the culturing, bulk production, formulation into a pharmaceutical and use of botulinum toxin. Important considerations are toxin purity and dose for injection. The production by culturing and the purification must be carried out so that the toxin is not exposed to any substance that might contaminate the final product in even trace amounts and cause undue reactions in the patient. These restrictions require culturing in simplified medium without the use of animal meat products and purification by procedures not involving synthetic solvents or resins. Preparation of toxin using enzymes, various exchangers, such as those present in chromatography columns and synthetic solvents, can introduce contaminants and are therefore excluded from preferred formulation steps. Furthermore, botulinum toxin type A is readily denatured at temperatures above 40 degrees Centigrade, loses toxicity when bubbles form at the air/liquid interface and denatures in the presence of nitrogen or carbon dioxide.

Particular difficulties exist to stabilize botulinum toxin type A, because type A consists of a toxin molecule of about 150 kD in noncovalent association with nontoxin proteins weighing about 750 kD. The nontoxin proteins are believed to preserve or help stabilize the secondary and tertiary structures upon which toxicity is dependant. Procedures or protocols applicable to the stabilization of nonproteins or to relatively smaller proteins are not applicable to the problems inherent with stabilization of the botulinum toxin complexes, such as the 900 kD botulinum toxin type A complex. Thus while from pH 3.5 to 6.8 the type A toxin and non toxin proteins are bound together noncovalently, under slightly alkaline conditions (pH>7.1) the very labile about 150 kD neurotoxic component of a botulinum toxin is released from the botulinum toxin complex. Xeomin™ is the trade name for a neurotoxic component botulinum toxin type A pharmaceutical composition available from Merz Pharmaceuticals (Frankfurt, Germany).

In some instances botulinum toxins, when used as therapeutic drugs, are known to migrate from the site of injection at various rates and distances, sometimes resulting in loss of effect at the desired muscle.

Solid botulinum toxin implants are known. See e.g., U.S. Pat. Nos. 6,306,423; 6,312,708, for a discussion of exemplary solid implants and applications. Additionally formulation of a botulinum toxin in a viscous carrier such as a hyaluronic acid is known; U.S. applications Ser. Nos. 11/954,629, and 11/954,602, filed Dec. 12, 2007.

What is needed is a biocompatible, gelable (thermoplastic) pharmaceutical composition comprising a stabilized botulinum toxin so that the composition can be administered as a liquid yet forms a sustained release gel upon administration; thereby localizing the effect and controlling release of the toxin to enhance the effect per dose.

SUMMARY

The present invention fulfills this need and provides a gelable, thermoreversible, thermoplastic botulinum toxin pharmaceutical composition that can be administered as a liquid and form a gel from which the botulinum toxin exhibits a sustained release upon administration of the pharmaceutical composition. Additionally, the present invention provides the additional advantage in that the compound which provides the thermo-reversible characteristic to the composition can also stabilize the botulinum toxin present in the pharmaceutical composition.

In one embodiment the present invention provides a thermoplastic thermoreversible, botulinum toxin pharmaceutical composition formulated with a poloxamer. Importantly, besides providing the thermoreversible, thermoplastic characteristics of the pharmaceutical composition the poloxamer can also act to stabilize the botulinum toxin.

DEFINITIONS

As used herein the words or terms set forth below have the following meaning.

"About" means that the item, parameter or term so qualified encompasses a range of plus or minus ten percent above and below the value of the stated item, parameter or term.

"Administration", or "to administer" means the step of giving (i.e. administering) a pharmaceutical composition to a subject. The pharmaceutical compositions disclosed herein are "locally administered" by e.g. intramuscular (i.m.), intradermal, subcutaneous administration, intrathecal administration, intraperitoneal (i.p.) administration, topical (transdermal) and implantation (i.e. of a slow-release device) routes of administration.

"Botulinum toxin" means: (1) a neurotoxin produced by *Clostridium botulinum*, as well as a botulinum toxin (or the light chain or the heavy chain thereof) made recombinantly by a non-Clostridial species; (2) the botulinum toxin serotypes A, B, C, D, E, F and G; (3) a botulinum toxin complex (i.e. the 300, 600 and 900 kDa complexes) as well as the neurotoxic component of a purified botulinum toxin (i.e. about 150 kDa), or; (4) a modified botulinum toxin, a pegylated (with a PEG), chimeric, recombinant, hybrid, wild-type botulinum toxins, botulinum toxin constructs, endopeptidases, chemically-modified botulinum toxins (pegylated botulinum toxin), and retargeted botulinum toxin, which retains the intracellular ability to inhibit acetylcholine release from a cell.

"Entirely free" (i.e. "consisting of" terminology) means that within the detection range of the instrument or process being used, the substance cannot be detected or its presence cannot be confirmed.

"Essentially free" (or "consisting essentially of") means that only trace amounts of the substance can be detected.

"Modified botulinum toxin" means a botulinum toxin that has had at least one of its amino acids deleted, modified, or replaced, as compared to a native botulinum toxin. Additionally, the modified botulinum toxin can be a recombinantly produced neurotoxin, or a derivative or fragment of a recombinantly made neurotoxin. A modified botulinum toxin retains at least one biological activity of the native botulinum toxin, such as, the ability to bind to a botulinum toxin receptor, or the ability to inhibit neurotransmitter release from a neuron. One example of a modified botulinum toxin is a botulinum toxin that has a light chain from one botulinum toxin serotype (such as serotype A), and a heavy chain from a different botulinum toxin serotype (such as serotype B). Another example of a modified botulinum toxin is a botulinum toxin coupled to a neurotransmitter, such as substance P.

"Pharmaceutical composition" means a formulation in which an active ingredient can be a Clostridial neurotoxin, such as a botulinum toxin. The word "formulation" means that there is at least one additional ingredient in the pharmaceutical composition besides a Clostridial neurotoxin active ingredient. A pharmaceutical composition is therefore a formulation which is suitable for diagnostic, therapeutic or cosmetic use (i.e. by intramuscular or subcutaneous injection or by insertion of a depot or implant or topical application) to a subject, such as a human patient. The pharmaceutical composition can be in a lyophilized or vacuum dried condition; a solution formed after reconstitution of the lyophilized or vacuum dried pharmaceutical composition with saline or water, or; as a solution which does not require reconstitution. As stated, a pharmaceutical composition can be liquid or solid, for example vacuum-dried. The constituent ingredients of a pharmaceutical composition can be included in a single composition (that is all the constituent ingredients, except for any required reconstitution fluid, are present at the time of initial compounding of the pharmaceutical composition) or as a two-component system, for example a vacuum-dried composition reconstituted with a diluent such as saline which diluent contains an ingredient not present in the initial compounding of the pharmaceutical composition. A two-component system provides the benefit of allowing incorporation of ingredients which are not sufficiently compatible for long-term shelf storage with the first component of the two component system. For example, the reconstitution vehicle or diluent may include a preservative which provides sufficient protection against microbial growth for the use period, for example one-week of refrigerated storage, but is not present during the two-year freezer storage period during which time it might degrade the toxin. Other ingredients, which may not be compatible with a Clostridial toxin or other ingredients for long periods of time, may be incorporated in this manner; that is, added in a second vehicle (i.e. in the reconstitution fluid) at the approximate time of use.

"Sustained release" means that the therapeutic agent (i.e. a botulinum toxin) contained by a pharmaceutical composition (such as a pharmaceutical composition comprising a poloxamer) is released from the pharmaceutical composition over a period of time between about 5 days and about 1 year.

"Stabilizer" (or "primary stabilizer") is a compound that assists to preserve or maintain the biological structure (i.e. the three dimensional conformation) and/or biological activity of a protein (such as a botulinum toxin). More than one stabilizer can be included in a pharmaceutical composition. Examples of stabilizers are surfactants, polymers, polyols, a poloxamer, albumin, gelatin, trehalose, proteins, sugars, polyvinylpyrrolidone, N-acetyl-tryptophan ("NAT")), caprylate (i.e. sodium caprylate), a polysorbate (i.e. P80), amino acids, and divalent metal cations such as zinc. A pharmaceutical composition can also include a preservative such as a benzyl alcohol, cresols, benzoic acid, phenol, parabens and sorbic acid.

"Stabilizing", "stabilizes", or "stabilization" mean that an active pharmaceutical ingredient ("API") retains at least 20% and up to 100% of its biological activity (which can be assessed as potency or as toxicity by an in vivo $LD_{50}$ or $ED_{50}$ measure) in the presence of a compound which is stabilizing, stabilizes or which provides stabilization to the API. For example, upon (1) preparation of serial dilutions from a bulk or stock solution, or (2) upon reconstitution with saline or water of a lyophilized, or vacuum dried botulinum toxin containing pharmaceutical composition which has been stored at or below about −2 degrees C. for between six months and four years, or (3) for an aqueous solution botulinum toxin containing pharmaceutical composition which has been stored at between about 2 degrees and about 8 degrees C. for from six months to four years, the botulinum toxin present in the reconstituted or aqueous solution pharmaceutical composition has (in the presence of a compound which is stabilizing, stabilizes or which provides stabilization to the API) greater than about 20% and up to about 100% of the potency or toxicity that the biologically active botulinum toxin had prior to being incorporated into the pharmaceutical composition.

"Substantially free" means present at a level of less than one percent by weight of the pharmaceutical composition.

"Therapeutic agent" means an active pharmaceutical ingredient (API) which can have therapeutic, cosmetic, and/or research use or benefit when administered to a patient. The therapeutic agent can be for example a steroid, antibiotic, or protein.

"Thermoplastic" is synonymous with "thermosensitive" and means a compound or composition which is a liquid or a low viscosity solution (i.e. viscosity less that 500 cps at 25° C. at a shear rate of about 0.1/second) at a low temperature (between about 0° C. to about 10° C.), but which is a higher viscosity ((i.e. viscosity less that 10,000 cps at 25° C. at a shear rate of about 0.1/second) gel at a higher temperature (between about 30° C. to about 40° C. such as at about 37° C.)

In particular embodiments, a thermoplastic, thermoreversible, pharmaceutical composition is disclosed comprising a biologically active botulinum toxin, and a thermoplastic poloxamer, where the poloxamer stabilizes the botulinum toxin so that the botulinum toxin retains biological activity upon release of the botulinum toxin from the pharmaceutical composition in vivo. The botulinum toxin is selected from the group consisting of the botulinum toxins types A, B, $C_1$, D, E, F and G and is preferably a botulinum toxin type A, known for its long lasting effect. An exemplary thermo-reversible poloxamer is a poloxamer 407, an example of which can be obtained from the BASF Corporation, Parsippany, N.J., under the name F-127.

In some embodiments, the poloxamer can be present at a concentration of from about 15 wt % to about 25 wt % of the pharmaceutical composition.

In one specific embodiment, the thermoreversible, thermoplastic, pharmaceutical composition comprises a biologically active botulinum toxin type A and a thermoplastic poloxamer 407 present at a concentration of about 15 wt % to about 25 wt % of the pharmaceutical composition, which stabilizes the botulinum toxin so that the botulinum toxin retains biological activity upon release of the botulinum toxin from the pharmaceutical composition in vivo.

A method for treating a medical or cosmetic condition is also disclosed herein, the method comprising the step of administering to a patient a thermoplastic, thermo-reversible pharmaceutical composition comprising a biologically active botulinum toxin and a thermoplastic, thermoreversible, poloxamer such that the poloxamer stabilizes the botulinum toxin so that the botulinum toxin retains biological activity upon release of the botulinum toxin from the pharmaceutical composition in vivo and the pharmaceutical composition is administered as a liquid and becomes a gel after the administration, to provide therapeutic amounts of the botulinum toxin released from the composition in vivo for at least 1 week after the administration. The thermoreversible, thermoplastic is a poloxamer 407 and is present at a concentration of about 15 wt % to about 25 wt % of the pharmaceutical composition. In some methods, a step of placing a cooling or heating element (such as, for example, a hot or cold pad, bottle, packet of ice or warm water and the like) is placed over an area of administration, before or after the administration step, in order to warm or cool the area to decrease or increase the viscosity of the administered thermoplastic, thermoreversible, pharmaceutical composition in situ and after its administration to the patient.

Exemplary medical conditions that can be so treated include glabellar lines, crows feet, marionette lines, nasolabial lines, horizontal lines of the forehead or any combination thereof. Additional exemplary medical or cosmetic conditions include treating at least one of overactive bladder, hyperhidrosis, benign prostatic hyperplasia and a dystonia, where the botulinum toxin is selected from the group consisting of the botulinum toxins types A, B, $C_1$, D, E, F and G. As above, the preferred botulinum toxin is botulinum toxin type A.

In particular embodiments, the botulinum toxin type A is present in the thermoreversible, thermoplastic, pharmaceutical composition in an amount from about 5 units to about 2750 units. The total amount (units) of a botulinum toxin to be administered to a patient is determined by the attending medical professional.

Also herein disclosed is a process for making a thermoreversible, thermoplastic, gelable, pharmaceutical composition, comprising the steps of dissolving a thermoplastic poloxamer in a solvent at a temperature below about 37 degrees Centigrade, adding and mixing a botulinum toxin to the thermoplastic poloxamer in the solvent to thoroughly disperse the botulinum toxin therein. The poloxamer can be present in particular embodiments at a concentration from about 15 wt % to about 25 wt % of the pharmaceutical composition, thereby making the thermoplastic, gelable, pharmaceutical composition.

In a particular process for making the thermoreversible, thermoplastic, gelable pharmaceutical composition, a botulinum toxin type A or B is utilized. An exemplary amount added can be from about 1 to about 2000 units of the botulinum toxin type A or from about 50 to about 25,000 units of a botulinum toxin type B, to be administered to a patient in need thereof. The process can also include adding an additive, for preservative or stabilizing purposes, for example, to form the final thermoplastic, gelable, pharmaceutical composition. In specific examples, the solvent utilized in the method of making the thermoplastic, gelable, pharmaceutical composition is water or a saline solution and the process of making the thermoplastic, gelable, pharmaceutical composition is carried out within a cold room having an temperature of below about 37 degrees Centigrade, or between about 0 to about 8 degrees Centigrade, for example.

Also disclosed are methods for treating a medical or cosmetic condition, that comprise the steps of administering to a patient a thermoreversible, thermoplastic, pharmaceutical composition that includes a biologically active botulinum toxin and a thermoreversible, thermoplastic poloxamer, wherein the poloxamer stabilizes the botulinum toxin and is a gel at room temperature (e.g the temperature of an enclosed space at which human beings are usually accustomed, e.g. from about 17° C. to about 25° C. Before administration, the pharmaceutical composition is cooled below the room temperature to reduce its viscosity (liquefy) the pharmaceutical composition and is thereafter drawn into a syringe and injected into the patient, where the thermoplastic pharmaceutical composition gels to deliver therapeutic amounts of the botulinum toxin are released from the composition in vivo for at least 1 week after administration. In particular embodiments, the thermoplastic poloxamer is a poloxamer 407 and is present at a concentration of about 15 wt % to about 25 wt % of the pharmaceutical composition.

The thermoplastic, pharmaceutical composition is thermoreversible, that is, its viscosity can be increased and/or decreased based on temperature, and is reversible. For example, the thermoreversible, thermoplastic poloxamer such as poloxamer 407 at about 20% wt (and hence the thermoplastic, pharmaceutical composition) can have a first viscosity at a first temperature (e.g. from about 0 centipoise (cP) at about 0 to about 16 degrees Centigrade), have its temperature raised to increase its viscosity to a second viscosity that is higher relative to the first viscosity (e.g. from about 50 cP to about 6000 cP at about 18 to about 22 degrees Centigrade), and then is reversible, e.g. lowering its temperature, decreasing its viscosity relative to the second viscosity, for example. A change in weight % of poloxamer 407 in a composition will alter its viscosity/temperature profile.

Each and every feature described herein, and each and every combination of two or more of such features, is included within the scope of the present invention, provided that the features included in such a combination are not mutually inconsistent.

DESCRIPTION

I have discovered new thermo-reversible depot pharmaceutical compositions (formulations) for a botulinum toxin. My invention is based on the discovery that certain thermoreversible poloxamers show remarkable compatibility with botulinum toxins. These depot systems can be thermally manipulated (pre & post injection) to control migration and distribution of the botulinum toxin. No combinations of botulinum toxins and poloxamer 407 are known.

A formulation within the scope of my invention is administered as a liquid and the polymer gels (cures) in situ at the site of local administration.

An embodiment of my invention can comprise a triblock PEO-PPO-PEO copolymer compounds, also known as pluronics or poloxamers, which at certain concentrations can form thermo-reversible gels which can be administered (as by injection) as a low viscosity liquid that rapidly increases in viscosity after injection. The resulting high viscosity matrix is adhesive, biodegradable and biocompatible and upon administration forms a depot from which the botulinum toxin can be released, thereby providing a sustained or extended release drug delivery system. In this manner a lower dose of the botulinum toxin can be used. Such a pharmaceutical composition can be administered pre-mixed or as a simple reconstitution vehicle or its several compartments combined at the time of administration, as by use of a dual chamber syringe.

I have found that botulinum neurotoxins are very stable in poloxamers, such as poloxamer 407, for example. This is surprising because of the complex structural nature of these toxins. For example, three separate protein domains (binding, translocation, enzymatic) must be conserved in order to maintain biological activity of the naked 150 kD toxin. Surfactants are chaotropic and therefore generally disrupt protein conformations. It is therefore surprising to find compatibility between these molecules and surfactants. The 900 kD toxins are protein complexes with neurotoxin associated proteins (NAPs), which stabilize the 150 kD portion. Surfactants would be expected to disrupt the protein complex, thereby destabilizing the complex and/or denaturing the 150 kD toxin portion.

The thermo-reversible poloxamer used in the present invention can apparently impart stability to a neurotoxin active ingredient, such as a botulinum toxin, present in the pharmaceutical composition by: (1) reducing adhesion (commonly referred to as "stickiness") of the botulinum toxin to surfaces, including the surfaces of laboratory glassware, vessels, the vial in which the pharmaceutical composition is reconstituted and the inside surface of the syringe used to inject the pharmaceutical composition. Adhesion of the botulinum toxin to surfaces can lead to loss of botulinum toxin and to denaturation of retained botulinum toxin, both of which reduce the toxicity of the botulinum toxin present in the pharmaceutical composition; (2) reducing the denaturation of the botulinum toxin and/or dissociation of the botulinum toxin from other non-toxin proteins present in the botulinum toxin complex, which denaturation and/or dissociation activities can occur because of the low dilution of the botulinum toxin present in the pharmaceutical composition (i.e. prior to lyophilization or vacuum drying) and in the reconstituted pharmaceutical composition; (3) reducing loss of botulinum toxin (i.e. due to denaturation or dissociation from non-toxin proteins in the complex) during the considerable pH and concentration changes which take place during preparation, processing and reconstitution of the pharmaceutical composition; (4) immobilizing the toxin in a high-viscosity vehicle; and (5) protecting the toxin from deleterious effects of elevated physiologic temperature (about 37° C.) and pH by providing a beneficial micro-environment.

The five types of botulinum toxin stabilizations provided by the poloxamers disclosed herein conserve and preserve the botulinum toxin and with it native toxicity of the toxin present in the pharmaceutical composition.

My invention also encompasses addition of a preservative, either in the diluent or formulation itself, to allow extended storage. A preferred preservative is preserved saline containing benzyl alcohol.

The thermo-reversible pharmaceutical compositions of the invention can be administered using conventional modes of administration. In particular embodiments of the invention, the compositions are administered intradermally, intramuscularly or subcutaneously to the patient. In addition, the compositions of the invention may be administered with one or more analgesic or anesthetic agents.

The most effective mode of administration and dosage regimen for the compositions of this invention depends upon the type, severity, and course of the condition being treated, the patient's health and response to treatment, and the judgment of the treating physician. Accordingly, the methods and dosages of the compositions can be tailored to the individual patient.

Compositions containing other serotypes of botulinum toxin may contain different doses (unit amounts) of the botulinum toxin. For example, botulinum toxin type B can be provided in a composition at a greater dose (about 50×) than a composition containing botulinum toxin type A. In one embodiment of the invention, botulinum toxin type B may be administered in an amount between about 1 U/kg and 150 U/kg. Botulinum toxin type B may also be administered in amounts of up to 20,000 U (mouse units, as described above). In another embodiment of the invention, botulinum toxin types E or F may be administered at concentrations between about 0.1 U/kg and 150 U/kg. In addition, in compositions containing more than one type of botulinum toxin, each type of botulinum toxin can be provided in a relatively smaller dose than the dose typically used for a single botulinum toxin serotype.

EXAMPLES

The following examples set forth specific embodiments of the present invention and are not intended to limit the scope of the invention.

In the Examples below the well known mouse lethal dose$_{50}$ assay (the "MLD50 assay") was used to determine the potency of the botulinum toxin released from the poloxamer formulations made. Depending on the circumstances, "potency" can mean the recovered potency of the botulinum toxin or the potency of the botulinum toxin prior to lyophilization. Recovered potency is synonymous with reconstitution potency, recovery potency and with potency upon reconstitution. The MLD50 assay provides a determination of the potency of a botulinum toxin in terms of its mouse 50% lethal dose or "LD50". Thus, one unit (U) of a botulinum toxin is defined as the amount of botulinum toxin which upon intraperitoneal injection kills 50% (i.e. a $LD_{50}$) of a group of female Swiss Weber mice weighing 17-22 grams each at the start of the assay. The MLD50 assay is a validated method for measuring the potency of a reconstituted botulinum toxin or of a reconstituted botulinum toxin formulation. Each mouse is held in a supine position with its head tilted down and is injected intraperitoneally into the lower right abdomen at an angle of about 30 degrees using a 25 to 27 gauge ⅜" to ⅝" needle with one of several serial dilutions of the botulinum toxin in normal saline. The death rates over the ensuing 72 hours for each dilution are recorded. A minimum of six dilutions at 1.33 dose intervals are prepared and typically ten animals are used in each dosage group (60 mice employed therefore). Two reference standard assays are carried out concurrently (additional 60 mice employed). The dilutions are prepared so that the most concentrated dilution produces a death rate of at least 80% of the mice injected, and the least concentration dilution produces a death rate no greater than 20% of the mice injected. There must be a minimum of four dilutions that fall within the monotone decreasing range of the death rates. The monotone decreasing range commences with a death rate of no less than 80%. Within the four or more monotone decreasing rates, the two largest and the two smallest rates must be decreasing (i.e. not equivalent). The dilution at which 50% of the mice die within the three day post injection observation period is defined as a dilution which comprises one unit (1 U) of the botulinum toxin. A refined MLD50 assay has been developed which uses fewer (five instead of six) dilutions at 1.15 dose intervals and fewer mice (six instead of ten) per dilution tested.

Example 1

Botulinum Toxin-Poloxamer 407 Formulations

Experiments were carried out in which a number of botulinum toxin-poloxamer formulations were made and assessed. The botulinum toxin used in each of the formulations made was lyophilized BOTOX®. The amount of the botulinum toxin used in each of the formulations made in 100 units of botulinum toxin type A (BOTOX®).

The poloxamer used in this example was poloxamer 407 obtained from BASF (Lutrol F-127). In each formulation, the poloxamer 407 was used in an amount that constituted 20 weight percent (wt %) of the final formulation. Poloxamer 407 is supplied as dry powder and is a hydrophilic non-ionic surfactant and a triblock copolymer consisting of two hydrophilic blocks (polyethylene glycol) separated by a hydrophobic block (poly-propylene glycol). The lengths of the two PEG blocks is about 101 repeating units, while the length of the propylene glycol block is about 56 repeating units. Solutions of Poloxamer 407, at appropriate concentrations, are liquid under refrigeration, but gel at room temperature and above (e.g., is a gel at about 37° C.). Poloxamer 407 can therefore be reconstituted or stored as a low-viscosity liquid for easy passage through a needle but then gels into a depot after injection into a mammal as it is subjected to increasing temperature. Poloxamer 407 was chosen for the formulations made in this example because of these desirable physical properties combined with unusual toxin compatibility.

Each formulation was made by a process which combines the solids (recall that the Poloxamer 407 is supplied as dry powder) in large centrifuge tubes with water or saline (inside a cold room at about 2 to about 8 degrees Centigrade) and is mixed with a magnetic stir bar, until fully dissolved.

The solutions are stored at from bout 4 to about 15 degrees Centigrade until injected/used. The solutions were then used to reconstitute a botulinum toxin type A (BOTOX®) in vials containing 100 units (U), by introducing the cold solution into the vials with a syringe.

Samples were then heated to 37° C. until gelled to simulate injection into a warm body.

Significantly I determined that the thermo-reversible formulations can be made with from 15-25 wt % poloxamer 407 (available from BASF as Lutrol F-127) without significant attenuation of the desired formulation characteristics of (1) thermoplasticity, and (2) sustained release of biologically active botulinum toxin from the formulations made.

As set forth below, 26 different thermo-reversible poloxamer formulations were made. Each of the 26 formulation made included 20 wt % poloxamer 407 and 100 units of botulinum toxin type A (BOTOX®):
1. 20% Poloxamer 407 in SWFI (sterile water for injection)
2. 20% Poloxamer 407 in 0.9% sodium chloride
3. 20% Poloxamer 407 in preserved (benzyl alcohol) 0.9% sodium chloride 4. 20% Poloxamer 407 with 5% Poloxamer 188
5. 20% Poloxamer 407 with 3% Tween
6. 20% Poloxamer 407 with 5% sucrose
7. 20% Poloxamer 407 with 5% dextran
8. 20% Poloxamer 407 in 10 mM histidine pH 7
9. 20% Poloxamer 407 in 20 mM citrate buffer pH 6
10. 20% Poloxamer 407 in phosphate buffered saline pH 7
11. 20% Poloxamer 407 with 20% propylene glycol
12. 20% Poloxamer 407 with 10% polyethylene glycol
13. 20% Poloxamer 407 with 20 mM Tris buffer pH 7
14. 20% Poloxamer 407 with 3% isopropyl myristate
15. 20% Poloxamer 407 with 5% povidone
16. 20% Poloxamer 407 with 3% lactose
17. 20% Poloxamer 407 with 3% trehalose
18. 20% Poloxamer 407 with 0.5% human serum albumin
19. 20% Poloxamer 407 with 0.5% human serum albumin 900 ug NaCl
20. 20% Poloxamer 407 with 0.5% recombinant human serum albumin
21. 20% Poloxamer 407 with 0.5% gelatin
22. 20% Poloxamer 407 with 0.5% recombinant gelatin
23. 20% Poloxamer 407 with 0.5% hyaluronic acid
24. 20% Poloxamer 407 with 0.5% collagen
25. 20% Poloxamer 407 with 2% hydroxypropyl methylcellulose
26. 20% Poloxamer 407 with 2% lecithin To determine that active botulinum toxin was released from each of the 26 thermo-reversible poloxamer formulations, light chain activity was measured using a fluorescent SNAP-25 substrate coupled with HPLC. Samples incubated with the substrate produce a cleavage product that is separated by RP-HPLC and detected via fluorescence. The amount of cleavage product is proportional to enzymatic activity.

Poloxamer 407 can be further manipulated pre and/or post-injection by applying heat or cold-packs to desired areas (injected and/or non-injected) achieve the desired effect. Additional ingredients can be added to the formulation to modify the attributes (causing increases/decreases in gelling temperatures, for example). Ingredients to alter osmolarity and pH (buffers) can be added. Administration can be topical rather than injectable; for example, in a transdermal delivery scheme, the formulation can contain permeation enhancers, and may be combined with a device such as a patch having additional permeation attributes, such as abrasives or microneedles, for example. Preservatives can also be included in the formulation. Colorants, such as pharmaceutically acceptable dyes, can be included to better visualize the material before and after application.

Example 2

Use of a Poloxamer-Botulinum Toxin Pharmaceutical Composition

A 48 year old male is diagnosed with a spastic muscle condition, such as cervical dystonia. Between about 50 to about 500 units of botulinum toxin type A (such as BOTOX®) combined with formulation 2 (20% Poloxamer 407 in 0.9% sodium chloride) in Example 1, and is administered by intramuscular injection. The formulation releases therapeutic amounts of the botulinum toxin over a 1 month period. Within 1-7 days the symptoms of the spastic muscle condition are alleviated and alleviation of the symptoms persists for at least about 6 months.

Example 3

Use of a Poloxamer-Botulinum Toxin Pharmaceutical Composition

A 22 year old female sees her physician to report and treat her uncontrollable and excessive armpit, sweating or as its known in the medical arts, axillary sweating. After gravimetric measurement of her sweat production, she is diagnosed as suffering from hyperhidrosis.

About 100 units of botulinum toxin type A (such as BOTOX®) is combined with formulation 12 (20% Poloxamer 407 with 10% polyethylene glycol) in Example 1, and is administered by intradermal injection into the axillary hyperhidrotic area (as determined by Minor's starch-iodine test). After injection, an ice pack is placed over the injected area, cooling the area and making the injected thermo-reversible poloxamer-botulinum toxin pharmaceutical composition less viscous, allowing the attending physician to massage the injected area, allowing a more even spread of the injected composition. Within 7 days, the excessive axial sweating is reduced and alleviation is observed for about 8 months.

Example 4

Use of a Poloxamer-Botulinum Toxin Pharmaceutical Composition

A 38 year old woman reports to her dermatologist that she can no longer withstand the sight of her glabellar lines (dynamic wrinkles between the brows caused by the contraction of corrugator and/or procerus muscles) and that they have become a source of great consternation. The dermatologist determines to treat her with a poloxamer-botulinum toxin pharmaceutical composition.

About 500 units of a botulinum toxin type B is combined with formulation 25 (20% Poloxamer 407 with 2% hydroxypropyl methylcellulose) in Example 1, and is administered by intramuscular injection directly into the corrugator and procerus muscles. Areas outside the desired treatment area are pre-heated (utilizing a heating pad to gradually warm the areas not injected, for example, from about 37 to about 43 degrees Centigrade, to elevate the temperature relative to the areas of injection) to prevent drug migration into those regions. Within about 7 days, the patient reports that the glabellar lines have been reduced and the skin between her brows is smoother. The alleviation of the wrinkles lasts for about 4 months.

Similarly, a botulinum toxin type A (BOTOX®) at about 2 units per 0.1 mL of added formulation can be injected at each of about 5 injection sites in corrugator and procerus muscles for a total dose of about 10 units per 0.5 mL of thermo-reversible poloxamer-botulinum toxin pharmaceutical composition. As an additional step, after or before injection into the muscles, a hot pad can be placed over the injection site to warm the area. Thus, if a hot pad is so placed, the injected poloxamer-botulinum toxin pharmaceutical composition can gel faster than if injected at just body temperature. The pad can be between about 37 degrees and about 43 degrees Centigrade, for example. The pad can be placed onto the area injected or to be injected and warmed up to between about 37 degrees and about 43 degrees Centigrade, for example.

Example 5

Use of a Poloxamer-Botulinum Toxin Pharmaceutical Composition

A 78 year old man is brought to his urologist, complaining of an inability to withhold his urine for any significant amount of time. The urologist determines that the patient is incontinent and has an overactive bladder (OAB) and that his detrusor muscle should be injected with a poloxamer-botulinum toxin pharmaceutical composition.

About 250 units of a botulinum toxin type A (BOTOX) is combined with formulation 2 (20% Poloxamer 407 in 0.9% sodium chloride) of Example 1 (about 250 units of toxin in about 10 mL of formulation 2). Utilizing a flexible cytoscope and standard bladder wall injection equipment (local anesthetic, lubricants, etc. ... ), the urologist proceeds to inject the patient's bladder wall at 10 sites (25 units/site) along the lateral walls, sparing the trigone and dome. Within about 7 days, the patient reports that he is able to hold his urine for many hours at a time, and that his voiding volume per visit to the urinal has more than doubled. The patient reports relief from his incontinence for approximately 7 months.

A bladder wall can also be injected with any one of the formulations (1-26) in Example 1 containing other botulinum toxin types, such as from about 50 to about 15,000 units of a botulinum toxin type B, utilizing from about 5 mL to about 30 mL of the formulations in Example 1. The thermo-reversible poloxamer-botulinum toxin pharmaceutical composition is injected into the bladder wall in about 5 to about 50 injection sites, as determined by an attending physician, and can include or exclude the trigone, if desired.

Example 6

Use of a Poloxamer-Botulinum Toxin Pharmaceutical Composition

A 67 year old man suffers from chronic urinary retention due to enlargement of his prostate. Upon presentation to his physician it is determined that the patient undergo administration of poloxamer-botulinum toxin pharmaceutical composition to the prostate in order to alleviate his urinary retention and treat the benign prostatic hyperplasia. About 200 units of botulinum toxin type A (BOTOX) is combined with 4 mL of formulation 2 (20% Poloxamer 407 in 0.9% sodium chloride) in Example 1 for transperineal injection into the bilateral lobes of the prostate (100 units per lobe).

After about 7 days, the patient reports an improvement in voiding of urine. His physician notes that after this treatment the patient has a decrease in post voiding residual volume and bladder pressure. These beneficial effects last for about 6 months and the physician notes that the patient's prostate has decreased in size and reports no adverse effects. A botulinum toxin type B (such as MYOBLOC) can also be utilized, for example, from about 250 units to about 1000 units per injection site.

A pharmaceutical composition according to the invention disclosed herein has many advantages, including the following:

1. the pharmaceutical composition can be prepared free of any blood product, such as albumin and therefore free of any blood product infectious element such as a prion.
2. the pharmaceutical composition has stability and high % recovery of toxin potency comparable to or superior to that achieved with currently available pharmaceutical compositions.
3. reduced toxicity, as assessed by either intramuscular or intravenous administration.
4. reduced antigenicity.

Various publications, patents and/or references have been cited herein, the contents of which are herein incorporated by reference in their entireties.

Although the present invention has been described in detail with regard to certain preferred methods, other embodiments, versions, and modifications within the scope of the present invention are possible. For example, a wide variety of stabilizing polysaccharides and amino acids are within the scope of the present invention.

Accordingly, the spirit and scope of the following claims should not be limited to the descriptions of the preferred embodiments set forth above.

I claim:

1. A method for treating a medical or cosmetic condition, the method comprising the step of
    administering to a patient a thermoreversible, thermoplastic, pharmaceutical composition consisting of a biologically active botulinum toxin type A present as a complex with human serum albumin and a thermoplastic poloxamer,
    wherein the thermoreversible, thermoplastic, pharmaceutical composition is transitionable from a low viscosity liquid solution for easy passage through a needle prior to administration by injection to a patient to a gel after administration.

2. The method of claim 1, wherein the thermoplastic poloxamer is a poloxamer 407.

3. The method of claim 1, wherein treating the medical or cosmetic condition comprises treating at least one of glabellar lines, nasolabial lines, crows feet, marionette lines and horizontal lines of the forehead.

4. The method of claim 1, wherein treating the medical or cosmetic condition comprises treating at least one of overactive bladder, hyperhidrosis, benign prostatic hyperplasia and a dystonia.

5. The method of claim 1, wherein the botulinum toxin type A is present in an amount from about 5 units to about 2750 units.

6. The method of claim 1, further comprising the step of placing a cooling or heating element over an area of administration before or after the administration step to warm or cool the area in order to decrease or increase the viscosity of the administered pharmaceutical composition, in situ, in the patient.

7. A method for treating a medical or cosmetic condition, the method comprising the steps of:
    administering to a patient a thermo-reversible thermoplastic,
pharmaceutical composition consisting a biologically active botulinum toxin type A present as a complex with human serum albumin, and a thermoreversible, thermoplastic poloxamer,
    wherein the poloxamer stabilizes the botulinum toxin so that the botulinum toxin retains biological activity upon release of the botulinum toxin from the pharmaceutical composition in vivo; and
    wherein the thermo-reversible, thermoplastic, pharmaceutical composition is transitionable from a low viscosity liquid solution for easy passage through a needle prior to administration by injection to a patient to a gel after administration.

8. The method of claim 7, wherein the poloxamier is a poloxamer 407.

9. The method of claim 7, wherein treating the medical or cosmetic condition comprises administration to at least one of glabellar lines, nasolabial lines, crows feet, marionette lines and horizontal lines of the forehead.

* * * * *